(12) United States Patent  (10) Patent No.: US 9,080,844 B2
Beauchamp et al.  (45) Date of Patent: Jul. 14, 2015

(54) LINKING OF MICROSCOPES FOR ANALYSIS OF OBJECTS COMPRISING TOOL MARKS

(75) Inventors: Alain Beauchamp, Montreal (CA); Danny Roberge, St-Bruno (CA); Benoit Perron, Boucherville (CA)

(73) Assignee: ULTRA ELECTRONICS FORENSIC TECHNOLOGY INC., Cote Saint-Luc (CA)

(*) Notice: Subject to any disclaimer, the term of this patent is extended or adjusted under 35 U.S.C. 154(b) by 284 days.

(21) Appl. No.: 13/098,758

(22) Filed: May 2, 2011

(65) Prior Publication Data

US 2011/0286090 A1    Nov. 24, 2011

Related U.S. Application Data

(60) Provisional application No. 61/330,604, filed on May 3, 2010.

(51) Int. Cl.
| | |
|---|---|
| G06K 9/60 | (2006.01) |
| F42B 35/00 | (2006.01) |
| G02B 21/18 | (2006.01) |
| G02B 21/36 | (2006.01) |
| G06T 7/00 | (2006.01) |
| G01N 15/14 | (2006.01) |
| G02B 21/00 | (2006.01) |

(52) U.S. Cl.
CPC .............. *F42B 35/00* (2013.01); *G02B 21/18* (2013.01); *G02B 21/365* (2013.01); *G06T 7/0028* (2013.01); *G01N 15/1475* (2013.01); *G02B 21/0016* (2013.01); *G06T 2207/10012* (2013.01); *G06T 2207/10021* (2013.01); *G06T 2207/10028* (2013.01); *G06T 2207/30136* (2013.01)

(58) Field of Classification Search
None
See application file for complete search history.

(56) References Cited

U.S. PATENT DOCUMENTS

| | | | | |
|---|---|---|---|---|
| 5,995,638 | A * | 11/1999 | Amidror et al. | 382/100 |
| 7,292,251 | B1 * | 11/2007 | Gu et al. | 345/555 |
| 2002/0085744 | A1 * | 7/2002 | Domanik et al. | 382/133 |
| 2004/0090671 | A1 * | 5/2004 | Gilbert | 359/391 |
| 2005/0117816 | A1 | 6/2005 | Saeger et al. | |
| 2009/0212242 | A1 * | 8/2009 | Yamada | 250/580 |

FOREIGN PATENT DOCUMENTS

CA    2722154    11/2009

OTHER PUBLICATIONS

International Search Report dated Aug. 8, 2011 issued by the International Bureau (WIPO) in connection with the corresponding International patent application No. PCT/CA2011/000521.

* cited by examiner

*Primary Examiner* — Ke Xiao
*Assistant Examiner* — Raffi Isanians
(74) *Attorney, Agent, or Firm* — Norton Rose Fulbright Canada LLP (57) ABSTRACT

There is provided a method for analyzing at least one object under a first microscope and a second microscope concurrently by linking the two microscopes together. Movement of one microscope will result in movement of the other. This is done by computing a transformation to link a first coordinate system and a second coordinate system and generating guidance data when one of the two microscopes is displaced, the guidance data corresponding to a set of operations to be applied to the other microscope to follow movement of the microscope that is displaced.

10 Claims, 9 Drawing Sheets

LINKING OF MICROSCOPES FOR ANALYSIS OF OBJECTS COMPRISING TOOL MARKS

CROSS-REFERENCE TO RELATED APPLICATIONS

This application claims priority of U.S. Provisional Patent Application No. 61/330,604, filed on May 3, 2010, the contents of which are all hereby incorporated by reference.

TECHNICAL FIELD

The present invention relates to the field of 3D image generation and visual ballistics identification.

BACKGROUND

In the field of forensic ballistics, microscopic tool marks present on different types of objects are compared to find matching tool marks to link the objects together, such as bullets that may eventually be linked to a recovered firearm. Comparisons are typically done using comparison microscopes, where an expert will visually compare the tool marks found on the two objects and use his experience to determine a match.

Some software tools exist to assist the expert in making the determination. For example, a 3D acquisition sensor can be used to acquire the topography, and possibly a 2D image, of an object with tool marks. Visual analysis of the resulting data can then be realized via a virtual comparison microscope which displays the acquired data.

A virtual comparison microscope is a software tool that displays the topography of one or several objects which may have tool marks. Its input is a list of virtual objects, each defined by a cloud of points in a 3D coordinate system which are connected in order to generate polygonal faces over the whole surface of the object. The minimal requirements of the virtual comparison microscope is the ability to display such clouds of points by using rendering techniques, move the virtual objects in space in translation (X, Y, translations) and rotation about any axis, zoom on the object, simulate different types of lighting conditions. The light source can be translated and rotated as well. Some virtual microscopes can also superpose a relevant texture on the virtual object. A virtual comparison microscope has some unique properties which are never met on a physical comparison microscope: an infinite depth of field, which removes any focus problems, and optimal design of the light source and reflectivity models, which brings a better control on the number of very bright or dark areas. However, the software tool is not used to make the final call. The expert must confirm potential matches using the comparison microscope.

A physical microscope has several limitations: finite depth of focus, non correspondence between the symmetry (or rotation) axis of the object, if any, and the rotation axis of the motor displacing the object, and independent rotation axes and light sources when two objects are analyzed at the same time.

Visual comparison of microscopic tool marks present on two objects under a comparison microscope may be significantly challenging, especially when only a few marks are present on the objects. In this case, the number of matching marks on any single region of interest may not be sufficient to state that the pair of analyzed objects is a "conclusive pair", i.e. a pair of objects which was in contact with the same tool or was fired with the same firearm. The tool mark or firearm expert must then look for groups of matching marks over several regions of interest.

This operation may be challenging due to limitations of the comparison microscope. This is especially true for bullets. In some instances, the bullets may have a circular cross section, i.e. a pristine form, and the symmetry axis of each bullet may coincide with the rotation axis when placed in the comparison microscope. In this case, the expert can compare the bullets by manually rotating each bullet around its corresponding rotation axis. However, in other instances, the symmetry axis and the rotation axis for one bullet may not coincide. The firearm expert must then apply several manual operations comprising rotating the bullets, translating the bullets and varying the position and intensity of the light sources in order to compare the two bullets. These operations are particularly challenging for bullets with very few small marks.

A further limitation of the physical comparison microscope is its finite depth of focus. When the topography in the field of view is not locally flat, it is not possible to analyze this whole area view with optical focus.

With such limitations, it is challenging and time consuming to look for matching marks between two objects with tool marks.

There is a need to improve the tools presently available to experts to facilitate the comparison that must be done using the comparison microscope.

SUMMARY

There is described a method for analyzing at least one object under a first microscope and a second microscope concurrently by linking the two microscopes together. Movement of one microscope will result in movement of the other. This is done by computing a transformation to link a first coordinate system and a second coordinate system and generating guidance data when one of the two microscopes is displaced, the guidance data corresponding to a set of operations to be applied to the other microscope to follow movement of the microscope that is displaced.

This method can be used to improve the comparison process in ballistics by linking a physical comparison microscope with a virtual comparison microscope, or by linking two microscopes of a same type together.

An expert may compare potentially matching regions from the digital data using a virtual microscope, and then analyze the corresponding regions with a conventional comparison microscope with the physical objects. A visual pre-analysis with a virtual comparison microscope allows the expert to select the best matching regions in a short amount of time. He can then focus on these few matching regions on the conventional comparison microscope for the final analysis.

By linking the operations done on the virtual microscope and the operations done on a motorized comparison microscope, this allows the selection of a given area of a digitized object on the virtual microscope that will lead to the corresponding area of the physical object under the conventional comparison microscope. Once the area is selected on the virtual microscope, two modes are then possible according to the level of automation of the comparison microscope: fully automated mode and hybrid manual/automated mode. A third system configuration (dual mode) incorporates both of these modes.

For a fully automated comparison microscope, the physical object installed on a motorized rotation axis may automatically move (by rotation and/or translation) so that the corresponding area appears within the field of view and in focus of the physical comparison microscope. For a hybrid manual/automated comparison microscope, the microscope may be equipped with encoders that report the current position of each axis, and the required motions of the physical bullet (rotation and/or translation) may be manually performed by the expert, based on guidance data. The guidance data may be updated periodically or continuously to guide the user during the manual operations until the selected area is at a predefined position in the field of view. A system adapted to function in both modes is also possible. Several strategies may be used to guide the users: displaying a number of translation and/or rotation steps to be applied in order to bring the corresponding area within the field of view of the comparison microscope, displaying graphical information, like directional arrows, using physical indicators like small light sources, etc.

The opposite process is also possible, whereby positioning the object under the physical comparison microscope leads to the corresponding region in the field of view of the comparison microscope to be displayed automatically by the virtual microscope. The digital data displayed by the virtual comparison microscope may follow the area within the field of view of the comparison microscope as the expert manipulates the object under the comparison microscope. This allows a parallel analysis of the digital data and the physical object.

According to a first broad aspect, there is provided a computer-implemented method for analyzing at least one object under a first microscope and a second microscope the method comprising: receiving a first set of position coordinates of the at least one object under the first microscope as a set of features on the at least one object are successively displayed within a field of view thereof, the first microscope having a first coordinate system; receiving a second set of position coordinates of the at least one object under the second microscope as a set of features on the at least one object are successively displayed within a field of view thereof, the second microscope having a second coordinate system; computing a transformation to link the first coordinate system and the second coordinate system using the first set of position coordinates and the second set of position coordinates; and generating guidance data when one of the first microscope and the second microscope is displaced, the guidance data corresponding to a set of operations to be applied to the other of the first microscope and the second microscope to follow movement of the one of the first microscope and the second microscope.

The first microscope and the second microscope may be virtual or physical. The operations may be done for two distinct objects, both installed on two distinct motorized rotation axes of a single physical microscope, and whose digital data is displayed by a virtual comparison microscope which allows two digital objects as inputs.

According to a second broad aspect, there is provided a system for analyzing at least one object microscopically, the system comprising: at least a first microscope and a second microscope, the first microscope having a first coordinate system and the second microscope having a second coordinate system; a computer system comprising a processor and a memory; and a microscope linking module stored on the memory and executable by the processor, the microscope linking module having program code that when executed, computes a transformation to link the first coordinate system and the second coordinate system, and generates guidance data when one of the first microscope and the second microscope is displaced, the guidance data corresponding to a set of operations to be applied to the other of the first microscope and the second microscope to follow movement of the one of the first microscope and the second microscope.

According to a third broad aspect, there is provided a computer readable memory having recorded thereon statements and instructions for execution by a computer to carry out a method for analyzing at least one object under a first microscope and a second microscope the method comprising: receiving a first set of position coordinates of the at least one object under the first microscope as a set of features on the at least one object are successively displayed within a field of view thereof, the first microscope having a first coordinate system; receiving a second set of position coordinates of the at least one object under the second microscope as a set of features on the at least one object are successively displayed within a field of view thereof, the second microscope having a second coordinate system; computing a transformation to link the first coordinate system and the second coordinate system using the first set of position coordinates and the second set of position coordinates; and generating guidance data when one of the first microscope and the second microscope is displaced, the guidance data corresponding to a set of operations to be applied to the other of the first microscope and the second microscope to follow movement of the one of the first microscope and the second microscope.

The term "object" refers to any object comprising tool marks which may be used as a Ballistic Piece of Evidence (BPOE). Examples of an object comprise a bullet or a portion of a bullet, a cartridge case, a gun barrel, a hammer, a screw driver, and the likes.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION

Visual comparison of microscopic tool marks present on two objects, each one under a physical microscope, may be done using the methods described herein. When the number of matching lines on any single region of interest is not sufficient to state that a pair of objects under analysis match, for example a pair of bullets fired from a same firearm, these objects may be translated and rotated together to other regions of interest to further compare the two and conclude on a match. Groups of matching lines over several regions of interest may then be used for the analysis.

In some embodiments, an alternative to visual analysis under a physical microscope consists in generating a 3D topography (and, possibly, a 2D image) for the object and visualizing the 3D topography on a virtual microscope. Different regions of interest of the object are scanned and a 3D topography image (and, possibly, a 2D image) is generated for each region of interest. Similarly to a physical microscope, the image of the object displayed on the virtual microscope may be displaced using translation and rotation movements in order to display the desired regions of interest. When comparing two objects on two virtual microscopes, the images of the objects are translated and rotated with respect to each other in order to find matching features between the two images.

Contrary to a physical microscope, a virtual microscope does not suffer from finite depth of focus and non correspondence between the symmetry (rotation) axis of the object, if any, and the rotation axis of the virtual motor displacing the virtual object. Furthermore, the 3D and possibly 2D data used to construct the rendered 3D model may be altered to maximize the ease of comparison for an expert examiner. Examples of alterations comprise the enhancement of microscopic details compared to the overall object's shape, the mapping of the microscopic texture of the object over a perfect cylinder surface and usage of idealized lighting geometry and reflection behavior. In addition, any of the techniques referred to in U.S. patent application Ser. No. 13/080,761 (the contents of which are hereby incorporated by reference) may also be used. However, the virtual microscope does not involve the direct observation of the physical object but the observation of a rendered virtual object from measured 3D and possibly 2D data.

When the pair of objects are analyzed using both a physical microscope and a virtual microscope, the coordinate systems of the virtual and physical microscopes are linked in order to have displacement of the image of an object on the virtual microscope cause a displacement of the object on the physical microscope, and vice versa.

In one embodiment, the user can manipulate both the virtual and the conventional microscopes in parallel. He may select a pair of matching regions (one region from object A and one region from object B) as seen on the virtual microscope and both physical objects under the physical microscopes will automatically follow to get the corresponding regions in the field of view of the physical microscopes. This process can be repeated over several pairs of matching regions as desired.

In some instances, the objects may have a circular cross section, i.e. a pristine form, and a symmetry axis of each object may coincide with a rotation axis when placed on a physical microscope. In other instances, the symmetry axis and the rotation axis for one object may not coincide. The methods described herein are adapted to deal with both of these situations.

Figure 1:
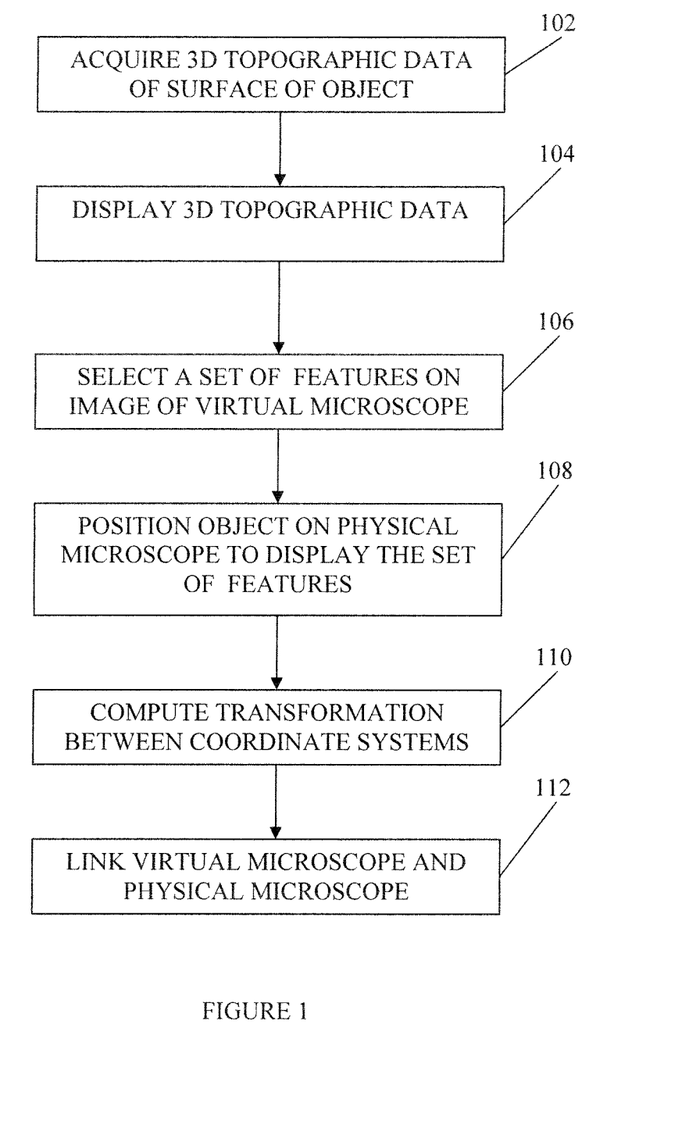
FIG. 1 is a flowchart illustrating a method for linking a virtual microscope and a physical microscope, in accordance with one embodiment.

FIG. 1 is a flowchart illustrating one embodiment of a method for linking a physical microscope and a virtual microscope for analysis of an object. The object has a macroscopic form and presents microscopic features, such as microscopic tool marks, on its surface. A first step 102 comprises acquiring 3D topographic data (x, y, z) of a surface of the object, thereby obtaining the microscopic and macroscopic features of the object. The acquisition can be done using any known sensors adapted to scan the object and acquired depth and surface information, such as laser profilometers, confocal microscopes, and others.

Figure 2:
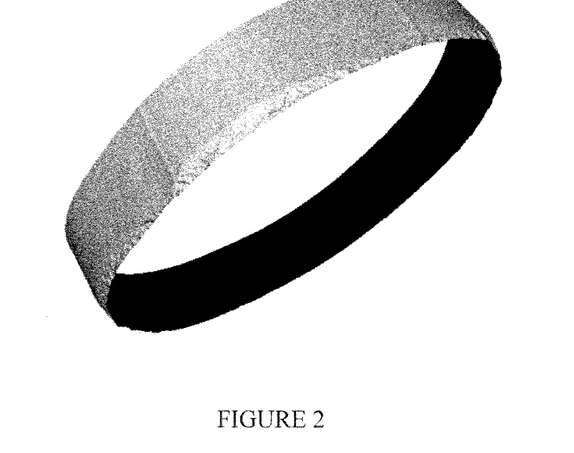
FIG. 2 is an exemplary illustration of the 3D topography of an object.

The acquired 3D topographic data is then displayed on the virtual microscope 104. FIG. 2 is an exemplary embodiment of the acquired 3D topographic data as displayed. The entire object may be scanned, or part of the object may be scanned, as illustrated in FIG. 2, resulting in a single ring of a bullet. On the image displayed, a set of features is selected from the 3D topography and this feature is positioned in the display window (or field of view) of the virtual microscope 106. As new features are selected, the user may have to manipulate the digital data, by applying rotation, translation or zoom. Selecting a given feature may comprise selecting a point having (x, y, z) coordinates, or a region including many points. This operation can be done by clicking on the feature on the screen with a mouse, by touching a touch screen at the position of the feature, or by other known methods.

The corresponding object is also positioned under a physical microscope such that each feature identified on the virtual microscope is successively displayed in the field of view of the physical microscope 108. This positioning may be done manually for each feature, by rotating and translating the stage of the physical microscope, or it may be done using a motorized axis and a software interface. The focus is automatically or manually adjusted in order to maximize contrast, and better define the Z position of the bullet.

Once both sets of features have been selected on the physical microscope and the virtual microscope, a transformation between the two coordinate systems is computed 110. The physical microscope has a physical coordinate system and the virtual microscope has a virtual coordinate system. This operation will be explained in more detail below.

The computed transformation from the virtual coordinate system to the physical coordinate system is then used to link the virtual microscope and the physical microscope 112 such that movement of the object under one of the two causes corresponding movement in the other one and/or generates guidance data to guide a user to perform the appropriate movements manually. In other words, movement of the object under one of the two microscopes causes a corresponding position for the other microscope to be generated, and either the other microscope is automatically moved to the corresponding position or specific instructions are given to a user to move the other microscope to the corresponding position.

The corresponding position for the physical microscope may be obtained by calculating the rotational and/or translational motion to apply to the motors controlling the stage of the physical microscope when the image on the virtual microscope is displaced. Similarly, when the motors are displaced to move the object on the physical microscope, the rotational and/or translational motion to apply to the image of the object on the virtual microscope may be calculated. The applied motions will then bring a selected feature into the field of view of one of the microscopes to match the feature in the field of view of the other one of the microscopes.

Figure 3:
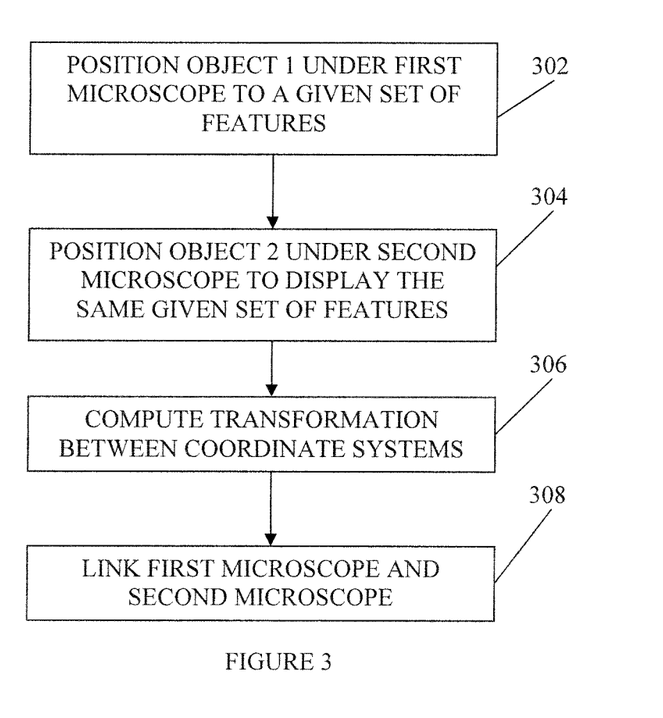
FIG. 3 is a flow chart illustrating a method for linking a first microscope with a second microscope of a same type, in accordance with one embodiment.

In one embodiment, the method may be used to link two microscopes of a same type, i.e. two virtual microscopes or two physical microscopes. The linking may be done directly (i.e. from one microscope to the other) or indirectly (i.e. via one or more microscope of a different type). FIG. 3a is a flowchart illustrating a method for directly linking a first microscope and a second microscope. This is done with either identical objects (or an object and its almost identical copy)

under both physical microscopes or a same 3D model of an object under both virtual microscopes. Techniques used to produce an almost identical copy of an object, such as those using various molds and materials such as resin, are known to those skilled in the art. In a first step, a first object is positioned in the first microscope such that a given set of features are successively displayed in the first microscope 302. Similarly, the second object is positioned in the second microscope such that the same given set of features are successively displayed in the second microscope 304.

The first microscope has a first coordinate system, while the second microscope has a second coordinate system. A transformation between the first coordinate system and the second coordinate system is computed 306. This transformation is computed using the set of positions of the first object in the first microscope and the set of positions of the second object in the second microscope. The first coordinate system and the second coordinate system are then linked 308 using the transformation such that movement of the object in one of the microscopes causes the generation of a set of movements (guidance data) necessary for the other microscope to follow. Once the two microscopes are linked in such a manner, different objects may then be viewed in each microscope. Having the two microscopes locked together then allows an expert to confirm a match between two different objects or two virtual models of different objects.

In another embodiment, the linking of two microscopes is done indirectly. For example, when linking a plurality of physical microscopes together (two or more), a 3D topography of the surface of each object is acquired. The physical microscopes are linked to their respective virtual microscopes, and then the virtual microscopes are linked together, thereby leading the physical microscopes to be linked together.

For two virtual microscopes, the first and second coordinate systems are both virtual coordinate systems dictated by the position of the respective object when placed on the rotation axis of a 3D acquisition system. For two physical microscopes, the first and second coordinate systems are both physical coordinate systems, differing due to the placement of the objects on a respective physical microscope.

In one embodiment, only subsets of the objects displayed in the virtual comparison microscope are linked. Thus, N objects could be displayed on the virtual comparison microscope, among which M<N objects would be linked to the corresponding physical object on the physical microscope. This allows the user to analyse the physical object using all relevant virtual models available even when some of the corresponding physical objects are not available. In some cases, there are more virtual models available for comparison than there are physical objects.

Figure 4:
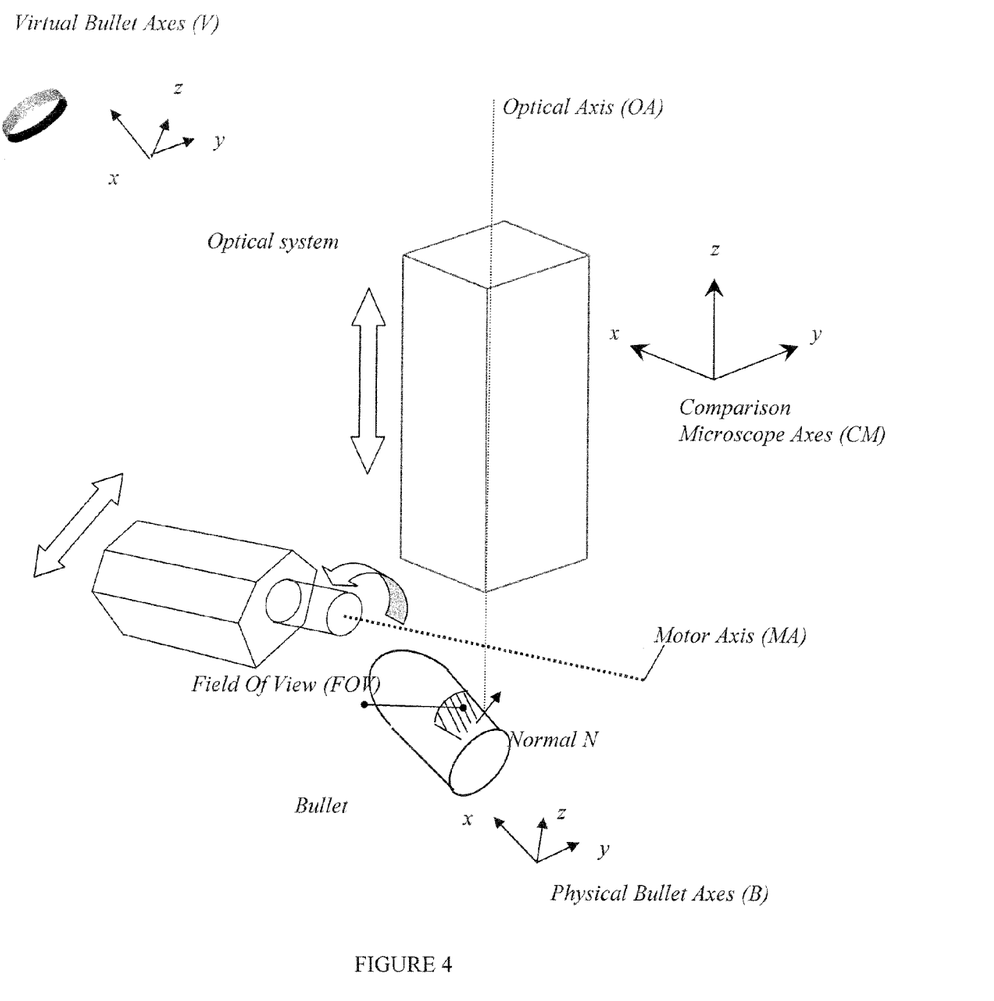
FIG. 4. illustrates a motorized physical microscope having a physical coordinate system and a motorized rotation axis in an arbitrary orientation with respect to the microscope, and an object installed on the rotation axis with an arbitrary orientation with respect to the rotation axis, in accordance with one embodiment.

Three systems of coordinates are involved in the derivation of the coordinate transformation that links the coordinates of the virtual object (or image of the object) in the virtual microscope and the coordinates of the physical object in the system of coordinates of the physical microscope, as described below. A bullet will be used as an exemplary object for the purposes of illustration. The first system is the intrinsic coordinate system of the physical bullet (B); the second is the coordinate system of the physical microscope (CM); the third is the coordinate system of the virtual bullet (V). The coordinate system B of the physical bullet is used for the derivation of the equation that links the two other coordinate systems; The three systems of coordinates are illustrated in FIG. 4.

The first system of coordinates is the intrinsic system of coordinates of the physical object (system B). The topography of the object is described by a fixed set of points R (XB, YB, ZB) in this coordinate system. For the case of a pristine bullet, the X_B axis is defined to be along its symmetry axis in FIG. 4. By definition, the coordinate XB, YB, ZB, of a given point of the physical bullet does not change as the bullet moves since this coordinate system follows the physical bullet.

The second system is the system of coordinates of the physical microscope (system CM). It is defined so as to coincide with the X-Y axis of the camera that acquires an image of the area under the microscope. Hence, the X=0, Y=0 position coincides with the (0,0) pixel of the image of the area within the field of view. The Z axis is defined as the axis perpendicular to the X and Y axes and along the optical axis of the microscope. The Z=0 position is defined upon initialization of the system as the vertical position of any point which is at the working distance from the microscope. Any point at that position yields an optimal contrast. FIG. 4 shows both coordinate systems (B and CM).

At initialization, the object is placed on the motorized rotation axis. There is no guaranty that the object is placed such that its symmetry axis (assuming a symmetric object) is perfectly along the direction of the motor axis. FIG. 4 illustrates this situation. In addition, the object may have been rotated or translated in any possible way before being placed on the motorized axis. Hence, a rotation by angle beta around an arbitrary axis characterized by a direction n and/or a translation S is applied to the object coordinates R in order to convert the position of a given point from the physical object coordinate system to the physical coordinate system of the microscope R':

R'=M[beta,n]R+S, where M is a rotation matrix which describes a rotation by an angle beta around a direction n, and S is a 3D vector which describes the translation. The parameters of this equation are fixed since it is assumed that the object never moves with respect to the rotation motor axis once it is placed there, the object having been firmly installed or fixed in some way.

A rotation by some angle alpha can then be applied around the rotation axis of the physical microscope. The rotation axis is characterized by a fixed normalized direction d and a crossing point A on the axis, both being unknowns at this point. The rotation operation can be represented by a matrix operation which is a function of angle alpha, direction d, and 3D vector A. The coordinates of a point R' on the object, in the CM system, is then transformed into R", as a result of the rotation:

R"=M[alpha,d](R'−A)+A. There is some redundancy in the position of the A vector. This point can be replaced by any other point on the rotation axis. Hence A may be replaced by A+lambda*d, where lambda is any real number, without changing the computed R" vector. This degree of freedom will be taken into account in a function minimization procedure that will be described below.

A translation T can also be applied either to the rotation axis or the microscope, and along any of the three possible coordinate axes (in the CM coordinate system). Whichever moves has no importance, as long as relative motion of the object/microscope components is allowed along the three axes. FIG. 4 shows the case where the rotation axis can be translated along X and Y, while the microscope can be translated vertically, along Z. As a result:

R'''=R"+T and, by combining previous equations,

R'''=M[alpha,d](M[beta,n]R+S−A)+A+T. Proper sign ± must be applied on each of the X, Y, Z components of the translation T according to the source of the motion, either the motorized axis which supports the bullet or the microscope.

It is assumed that the coordinate R'''=(X''', Y''', Z''') of any point of the object in the physical microscope coordinate system can be selected from the data in the field of view of the physical microscope. For example, by clicking on a live image of the data in the field of view, the X''' and Y''' coordinates can be defined. Furthermore, by doing a search for the best focus at that pixel point, a Z''' coordinate can be defined. In the above equation, the known parameters are the translation vector T, the rotation angle alpha and the selected vector position R'''; the unknowns are the direction d and axis origin vector A, but also the initial positioning of the object on the rotation motor axis, defined by an angle beta, a direction n and a translation vector S.

The third coordinate system is the system of coordinates of the virtual object. The digitized representation of the object, used in the virtual microscope, is stored as a set of 3D points P which are fixed in the virtual coordinate system. It is assumed that the object used in the virtual microscope corresponds to the object in the physical one.

It is further assumed that coordinates of any point P of the virtual object can be selected by a user, for example by clicking on that point on the screen of the virtual microscope. The normal N, that is, the direction which is locally perpendicular to P, is also available. If not, it can be computed with known methods based on the digitized topography in a neighbourhood of P. It is assumed that the normal points along the outward direction, i.e., out of the object, and not towards the interior of the surface.

There is no guaranty that a given point of the digitized object, with coordinate P in the virtual coordinate system (V), has the same coordinates as the corresponding point R on the real object in its own coordinate system (B). However, there must be some linear transformation between them. It is assumed that no change of scale is involved. The assumed transformation is then a combination of a rotation by angle gamma around an axis with direction m and a translation Q. The parameters m, gamma and Q in this transformation are unknowns, but they are fixed, even if the digitized and real objects move on the virtual and physical comparison microscopes, respectively. The point P is known since it has been selected by the user on the virtual microscope. The relation between R and P is then:

R=M[gamma, m]P+Q, where M is a rotation matrix which describes a rotation by angle gamma around a direction m, and Q is a 3D vector which describes the translation.

A relation between two known vectors, P and R''', is generated by substituting the last equation in the previous one:

$$R=M[alpha,d](M[beta,n](M[gamma,m]P+Q)+S-A)+A+T$$

At this point, the user selects N points with coordinates P on the virtual microscope, which correspond to N points with coordinates R'''=(X''', Y''', Z''') in the physical microscope coordinate system. The X''' and Y''' coordinates (in physical units, like micron or mm) are computed from the known pixel position of the point from the image acquired by the camera. It is assumed that the bullet and/or microscope have been translated along the Z direction in order to bring optimal focus at that point. Thus, the Z''' component of the point is 0 by definition. The following scalars and vectors remain constant: gamma, m, Q, beta, n, S and d. The following parameters change between selected points: alpha, the angle of rotation of the real object around the motorized axis of the physical microscope, and the translation T of the axis. However, they are both available from the software application which controls the motorized axis of the physical microscope or from the encoders of a non motorized microscope. For each of these pairs of points, the following vector equation should be satisfied:

$$R'''\_i=M[alpha\_i,d](M[beta,n](M[gamma,m]P\_i+Q)+S-A)+A+T\_i,$$

where the integer index i ranges from 1 to N, N being the number of defined pairs of points.

Since the product of matrices M(beta, n) and M(gamma, m) is unknown but fixed, and since similarly the vector which results from the operation M(beta, n)Q+S is unknown but fixed, and since, furthermore, these matrices and vectors do not appear in other combinations, they can be replaced by a new rotation matrix M(delta, g) and vector U, respectively, both unknown and fixed:

$$R'''\_i=M[alpha\_i,d](M[delta,g]P\_i+U-A)+A+T\_i.$$

After an algebraic manipulation, this equation becomes:

$$M[alpha\_i,d](M[delta,g]P\_i+U-A)+A+T\_i-R'''\_i=0.$$

In practice, the above equation is never perfectly satisfied. However, the unknown parameters (angle delta, direction g, vector U, direction d, vector A) can be found by minimizing a non-negative function which vanishes if and only if the above vector equation is simultaneously satisfied for all N selected points, and which is an increasing function of the norm of the left side of this vector equation, for all N selected points.

Any function satisfying this condition can be chosen. One simple such function is the sum of the square norm of the vector equation above over all N points:

$$F = \sum_{i=1}^{N} \sum_{j=1}^{3} |M[alpha\_i, d](M[delta, g]P\_i + U - A) + A + T\_i - R'''\_i|_j^2$$

where i is an index running over the points and j runs over the three coordinates, x, y, z.

The equation above may be generalized in the case where the measurement error changes according to the three axes x-y-z, by adding a weight that characterizes measurement errors along each axis:

$$F = \sum_{i=1}^{N} \sum_{j=1}^{3} w_j |M[alpha\_i, d](M[delta, g]P\_i + U - A) + A + T\_i - R'''\_i|_j^2$$

In the proposed method, the X and Y coordinates of R''', on one hand, and its Z coordinate, on the other hand, are found by distinct operations: selecting a pixel on screen for X and Y, and searching for the optimized focus for Z. Measurement errors are expected to be different for both techniques. This is dealt with using the appropriate weight in the previous equation.

As discussed previously, the vector A can be replaced by any other point on the rotation axis with direction d, that is, by A+lambda d, where lambda is any real number. The original minimization procedure is therefore equivalent to minimize $$F = \sum_{i=1}^{N} \sum_{j=1}^{3} w_j$$

$$|M[alpha\_i, d](M[delta, g]P\_i + U - A - \lambda d) + A + \lambda d + T\_i - R'''\_i|_j^2$$

where lambda is a free parameter that has no impact on the value of F. This degree of freedom may generate ill-defined behaviour of the minimization procedure since the parameters to be searched for are not all independent. The solution is to adopt a convenient value for lambda. Two simple choices are available: i) lambda can be chosen so that U−A+lambda*d is perpendicular to d, or ii) lambda can be chosen so that A+lambda*d is perpendicular to d. The final function to minimize can then be written in the form $$F = \sum_{i=1}^{N} \sum_{j=1}^{3} w_j |M[\text{alpha\_i}, d](M[\text{delta}, g]P\_i + V) + C + T\_i - R'''\_i|_j^2$$

where V and C are two vectors, and where V or C is constrained to be perpendicular to d (V has the constraint with choice i); C has it with choice ii). We therefore assume that the following equation is approximately satisfied:

$M[\text{alpha}\_i,d](M[\text{delta},g]P\_i+V)+C+T\_i=R'''\_i$

In the following example, we will adopt the second choice, but both are equally valid. The number of independent parameters to be found by the minimization procedure is therefore 10, that is, 1 (angle delta)+2 (direction g, unit-norm)+2 (vector C with one constraint)+2 (direction d, unit-norm)+3 (vector V).

Such non-linear minimization problems can be solved by iterative techniques like the Levenberg-Marquardt technique, steepest descent methods, simulated annealing, genetic algorithms or brute force search within the parameter space, or any other known methods. Since there may be several local minima, the global minimum might be found only by using some of the iterative techniques with a list of several starting points. The constraints on g, d and V can also be treated using different techniques. The directions g and d can be defined with 3 Cartesian coordinates, in which case two Lagrange multipliers are added to the function to be minimized in order to force the norm of these vectors to unity. These two vectors can also be described by a unit norm vector in radial coordinates with a pair of elevation and azimuth angles (theta, phi). Both strategies are valid. Similarly, the vector C can be defined with three Cartesian coordinates, in which case one Lagrange multiplier is added to the function to be minimized in order to make C perpendicular to d. The vector C can also be described by only two independent parameters which are the weights in a linear combination of two unit-norm vectors perpendicular to each other and perpendicular to d.

Once the parameters are known with reasonable accuracy from the fitting procedure, the two microscopes are linked.

The user can then select a point P (and its associated unit-norm outward-pointing local normal N) on the virtual microscope and compute vectors Q1=(M[delta,g]P+V) and Q2=M[delta,g]N. The rotation alpha and translation T required to bring the corresponding point of the real object in the field of view (for example in the center of the field of view) must satisfy the X and Y components of the following vector equation: R'''=M[alpha,d]Q1+C+T, where the X and Y coordinates are the position of the central pixel of the display (converted into physical units, micron or mm).

This is a set of two equations in three unknowns (rotation alpha and the X-Y components of the translation vector T). The additional constraint is given by forcing the rotation to bring the local normal N''' of the topography along the microscope vertical axis, that is, the Z axis, as much as possible. This geometric configuration optimizes the visual analysis. Thus the angle between the Z axis and the local normal is minimized. Equivalently, the dot product of the Z vector (0, 0, 1) and the unit norm N'''=M[alpha,d]Q2 is maximized.

Known techniques can be used to find the optimal angle alpha from this condition. The angle value is then substituted in the equation for R''' in order to solve for the X-Y components T.

The Z component of the translation can then be found in two possible ways, if not done manually: 1) automatically adjusted in order to maximize contrast; 2) by substituting the alpha angle value previously computed and the current Z component of the bullet/microscope position in the R''' equation; the Z-translation to be applied is then found from the known working distance of the microscope.

The user can also rotate and translate the physical object, by an angle alpha and a vector T, respectively, and select a point R'''=(X''', Y''', Z'''). The X''' and Y''' coordinates of the point are found from the live image of the area currently in the field of view of the physical comparison microscope and displayed on screen. It is assumed that a translation T has been applied along the Z direction to bring the point at the best focus position. The Z''' coordinate is therefore defined as 0. The corresponding point P* in the virtual bullet representation is then found as a function of R''' as follows, by inversion of the equation that finds R''' from a known point P: P*=M[−delta,g](M[−alpha,d](R'''−C−T)−V). The computed value P* will in general be different than any of the P points which define the virtual model. The adopted P point should be the one, within the list, which is nearest to P*, as measured by the Euclidean distance, for example. The virtual object can then be rotated and/or translated in order to bring that point (P) to some predefined position on the screen of the virtual microscope, for example at the center of the screen and with a predefined orientation for its local normal.

A unique zoom factor is assumed in the previous derivation of the method. However, the latter can be generalized for a system which offers several predetermined zoom positions. A linear relationship between the pixel coordinates at two different zooms can be determined at initialization:

$x(\text{Zoom 1})-x\text{Center}=K[x(\text{Zoom 2})-x\text{Center}]$ $y(\text{Zoom 1})-y\text{Center}=K[y(\text{Zoom 2})-y\text{Center}]$ where x(Zoom1) and x(Zoom2) are the x component of the pixel coordinates of a point on an object lying under the microscope at Zoom1 and Zoom2 respectively, and xCenter is the pixel coordinate at the center of the display. The K term is the ratio between the zoom factors. It is assumed that the system has been properly calibrated so that a point on an object displayed at the center of the screen remains at the center if the zoom is changed. There is also a linear relationship for the best focus position:

$z(\text{Zoom1})=[z(\text{Zoom 2})-\Delta]$ where $\Delta$ is the difference between the working distance at the two zoom positions.

Figure 5:
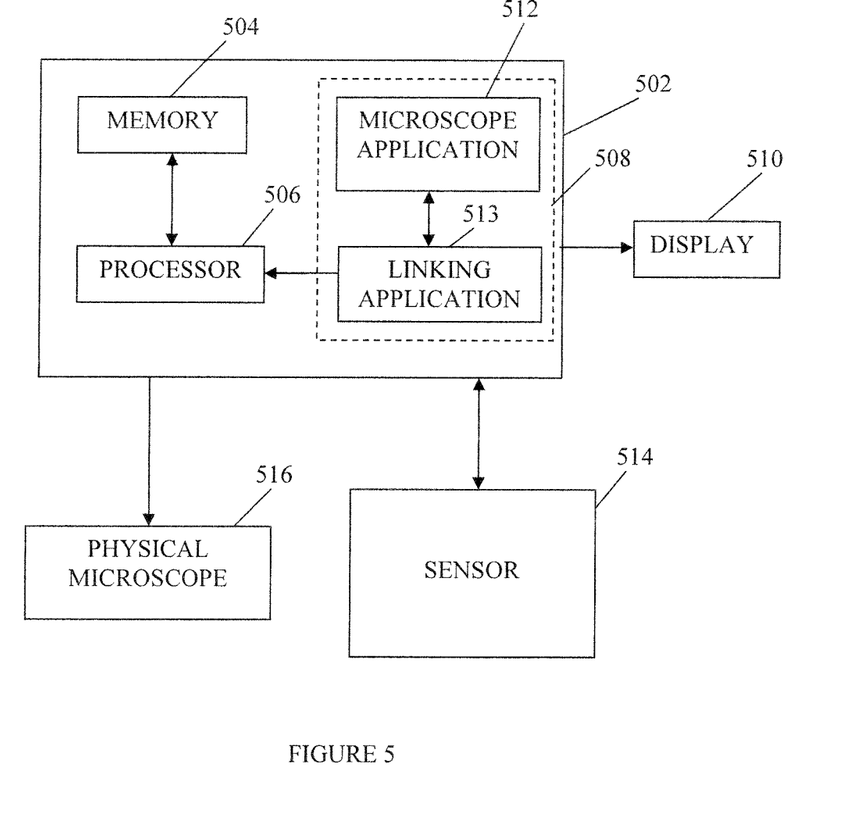
FIG. 5 is a block diagram illustrating a 3D acquisition and viewing system, in accordance with one embodiment.

FIG. 5 illustrates an exemplary embodiment for a 3D image acquisition system having an application for linking microscopes together. A computer system 502 comprises an application 508 running on a processor 506, the processor being coupled to a memory 504. A sensor 514 and a display 510 are connected to the computer system 502.

The memory 504 accessible by the processor 506 receives and stores data, such as acquired images, (x, y, z) topographies, 3D coordinates, and any other information used by the 3D image acquisition system. The memory 504 may be a main memory, such as a high speed Random Access Memory (RAM), or an auxiliary storage unit, such as a hard disk, a floppy disk, or a magnetic tape drive. The memory may be any other type of memory, such as a Read-Only Memory (ROM), or optical storage media such as a videodisc and a compact disc.

The processor 506 may access the memory 504 to retrieve data. The processor 506 may be any device that can perform operations on data. Examples are a central processing unit (CPU), a front-end processor, a microprocessor, a graphics processing unit (GPU/VPU), a physics processing unit (PPU), a digital signal processor, and a network processor. The application 508 is coupled to the processor 506 and configured to perform various tasks as explained below in more detail. An output may be transmitted to a display device 510.

In one embodiment, the computer system 502 is integrated directly into the sensor 514 while in another embodiment, the computer system 502 is external to the sensor 514. The sensor 514 may communicate with the computer system 502 in a wired or wireless manner.

In one embodiment, the application 508 comprises a microscope application 512 that communicates with a linking application 513. For example, the microscope application 512 may be responsible for controlling the motors of the physical microscope. Once the linking application 513 computes the translational and rotational displacements for the motors, they are sent to the microscope application 512. The application 508, or statements and instructions for execution by the processor 506, may be embodied on any type of computer readable medium, whether it be integrated inside the computer system 502 or external thereto.

In one embodiment, launching of the linking application 513 will cause the computer system 502 to ask a user, via a user interface such as display 510, to input certain parameters, position the objects under analysis, and/or select features of interest on a screen or display 510. Once the actions have been taken by the user, the computer system 502 will then automatically calculate the transformation to link two microscopes together and apply the transformation as needed.

In one embodiment, a plurality of physical microscopes may be used with a single virtual microscope having multiple viewers for displaying corresponding images of objects under observation in the physical microscopes. Alternatively, each physical microscope may operate with its own virtual microscope. In addition, dual-stage microscopes may be used (microscopes capable of holding two objects at once), leading to a ratio of N virtual microscope or viewers to N/2 physical microscopes.

The differences in coordinate systems, whether it be between a virtual microscope and a physical microscope, two virtual microscopes, or two physical microscopes, can be due to a variety of factors. One possible factor is the positioning of the object on the axis of rotation of a 3D acquisition system. Another factor is the orientation of the axis of rotation of the 3D acquisition system. Yet another factor is the positioning of the object on the axis of rotation of the physical microscope, and finally, the orientation of the axis of rotation of the physical microscope.

Figure 6:
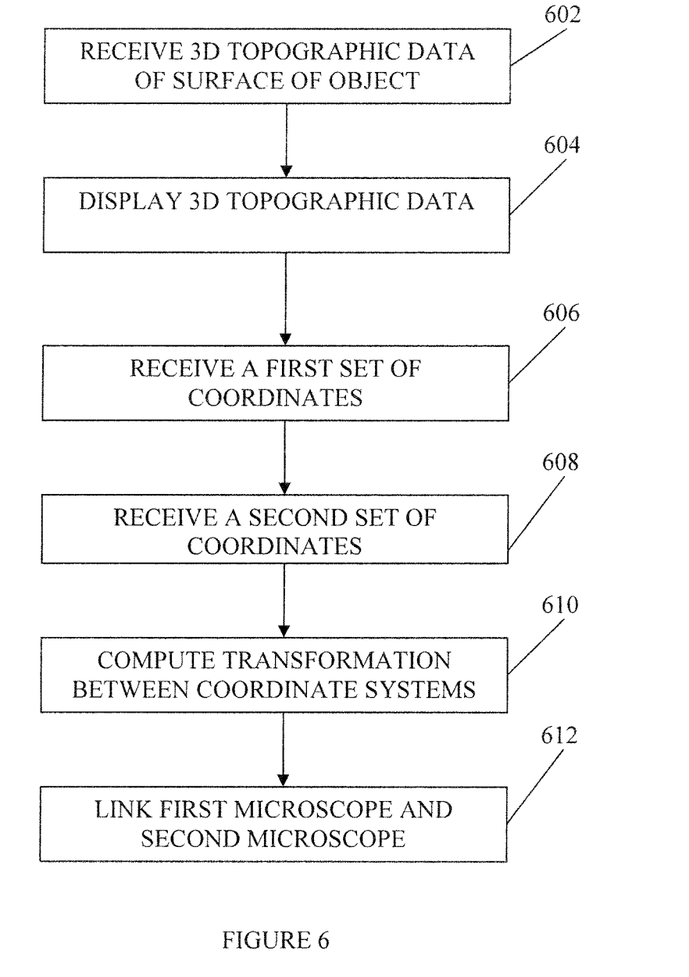
FIG. 6 is a flowchart illustrating a computer-implemented method for linking a virtual microscope and a physical microscope, in accordance with one embodiment.

FIG. 6 is a flowchart illustrating a computer-implemented method, as carried out by the computer system 502, for linking a physical microscope and a virtual microscope for analysis of an object. The 3D topographic data is received 602 and may be stored in the memory 504 or used immediately by the application 508. The 3D topographic data is displayed 604 on a display device 510.

A first set of coordinates representative of selected features of the 3D topographic data on the virtual microscope is received 606 by the computer system 502. A second set of coordinates representative of the positions of the physical microscope when the object is positioned to display the selected features on the physical microscope is also received 608 by the computer system 502. The first and second sets of coordinates may also be stored in the memory 504.

On the basis of the sets of coordinates, a transformation is computed 610 to link the virtual coordinate system and the physical coordinate system. The virtual coordinate system and the physical coordinate system are then linked using the transformation 612, such that movement of the object under one of the two causes corresponding movement in the other one. As indicated above, in one embodiment actual movement of the second microscope is not automated. Guidance data is generated and provided to a user to allow manual movement of the second microscope.

Figure 7:
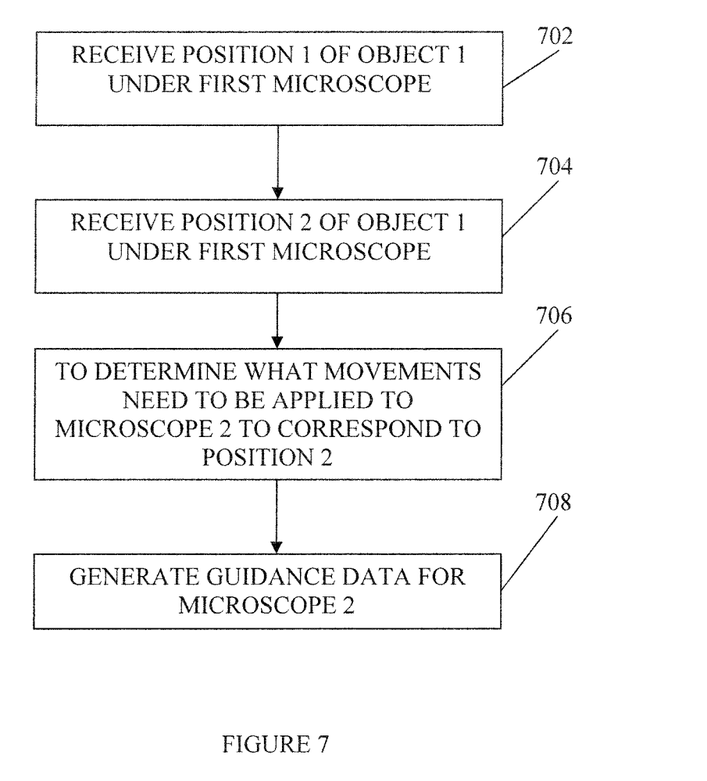
FIG. 7 is a flowchart illustrating a computer-implemented method for an object with a first microscope and a second microscope, in accordance with one embodiment.

FIG. 7 is a flowchart illustrating a computer-implemented method as carried out by the computer system 502, for analysis of a pair of objects concurrently under a first microscope and a second microscope, the pair of objects having common features and the microscopes having been linked, as per the method described with reference to FIG. 3. The computer system 502 receives a first set of coordinates 702 for the first object positioned in the first microscope. The computer system 502 also receives a second set of coordinates 704 when the first object is moved to a second position in the first microscope.

The application 508 determines what movements (rotations and/or translations) are needed in the second coordinate system to position the second object at the second position 706. The application 508 can then generate guidance data 708 that when applied to the second microscope causes movement of the second microscope corresponding to movement of the first microscope. In one embodiment, the guidance data is used to automatically move the second microscope. In another embodiment, the guidance data is provided to the user and the user follows the rotation and/or translation instructions to move the second microscope.

Figure 8:
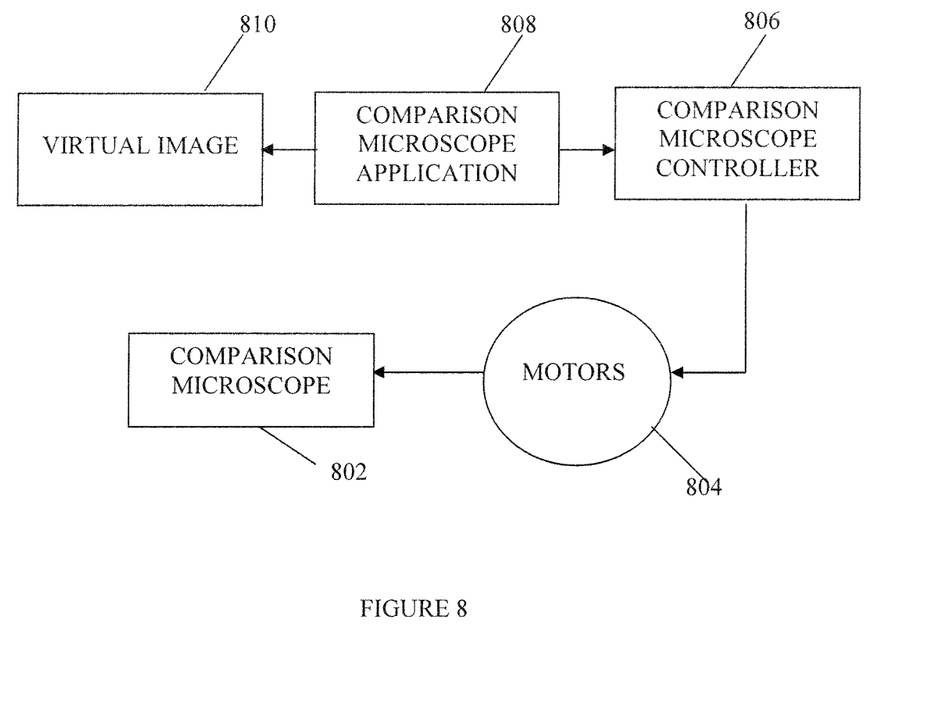
FIG. 8 is a block diagram illustrating a fully automated system.

FIG. 8 is a block diagram illustrating the system which corresponds to a fully automated comparison microscope. The user selects points on the physical object in the field of view of the comparison microscope 802 using the comparison microscope software application 808 (with some form of input device, like a mouse, keyboard and/or joystick) and selects matching points in the virtual image 810, also using the microscope software application 808. The virtual image and the physical microscope 802 are then linked using the above-described method. When the user moves the object on the comparison microscope using the comparison microscope software application 808, the virtual image 810 moves automatically. When the user moves the virtual image 810, the object in the physical comparison microscope 802 automatically moves to the corresponding position. A microcontroller 806 is the interface between the physical comparison microscope 802 and the comparison microscope software application 808. This component is able to translate software actions into physical motion and vice versa. A set of motors 804 are used to perform the displacement of the object in the comparison microscope 802.

Figure 9:
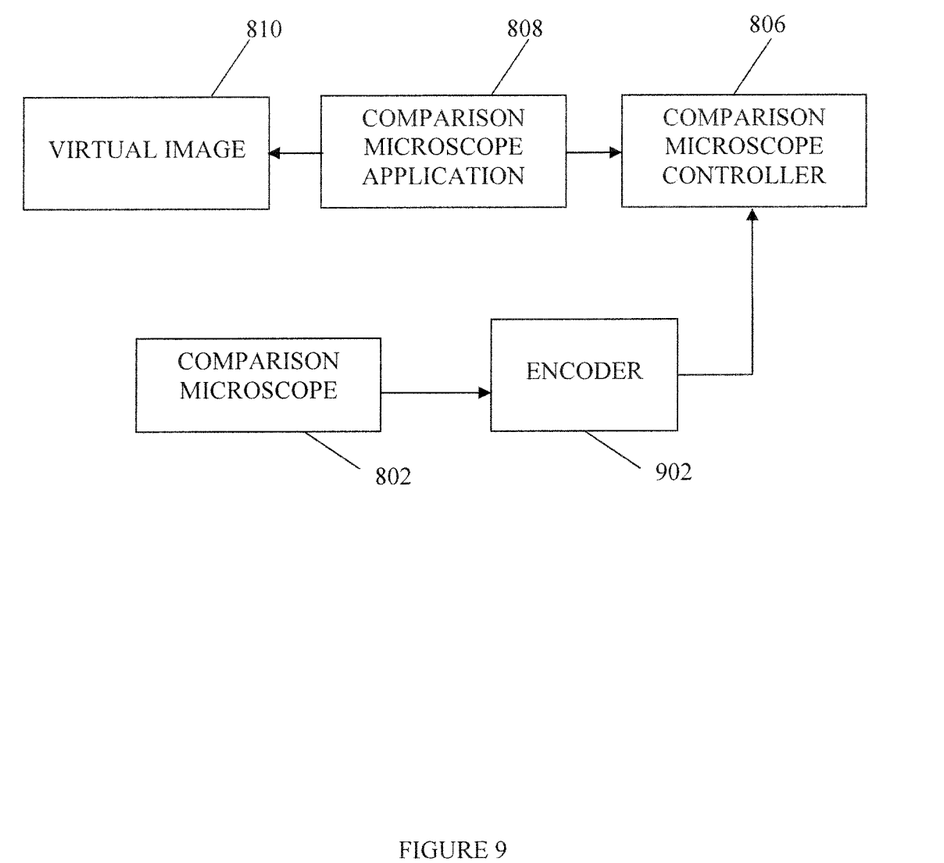
FIG. 9 is a block diagram illustrating a hybrid manual/automated system.

FIG. 9 illustrates the system which corresponds to a non automated comparison microscope, also called a hybrid manual/automated system. The user manually selects points on the object on the physical comparison microscope 802 and matching points in the virtual image 810 using the comparison microscope application 808. The virtual image 810 and the physical microscope 802 are then linked using the above-described method. When the user manually moves the object on the comparison microscope 802, the virtual image 810 moves automatically. When the user moves the virtual image 810, the comparison microscope application 808 determines what the corresponding moves need to be applied to the comparison microscope 802 and indicates to the user what axes need to be operated, in which direction and by what amount, using indicators. The comparison microscope controller 806 then continuously monitors the data from the encoders 902 and notifies the user about the state of every axis.

When the user moves the object in the comparison microscope 802, the position of each axis of the object/comparison microscope is reported to the comparison microscope application 808 through the controller 806. This allows the comparison microscope application 808 to synchronize with the manually operated physical comparison microscope 802. As most firearm experts currently use non motorized comparison microscopes, the synchronization of the physical and virtual models may be easier to do in manual mode for them.

Figure 10:
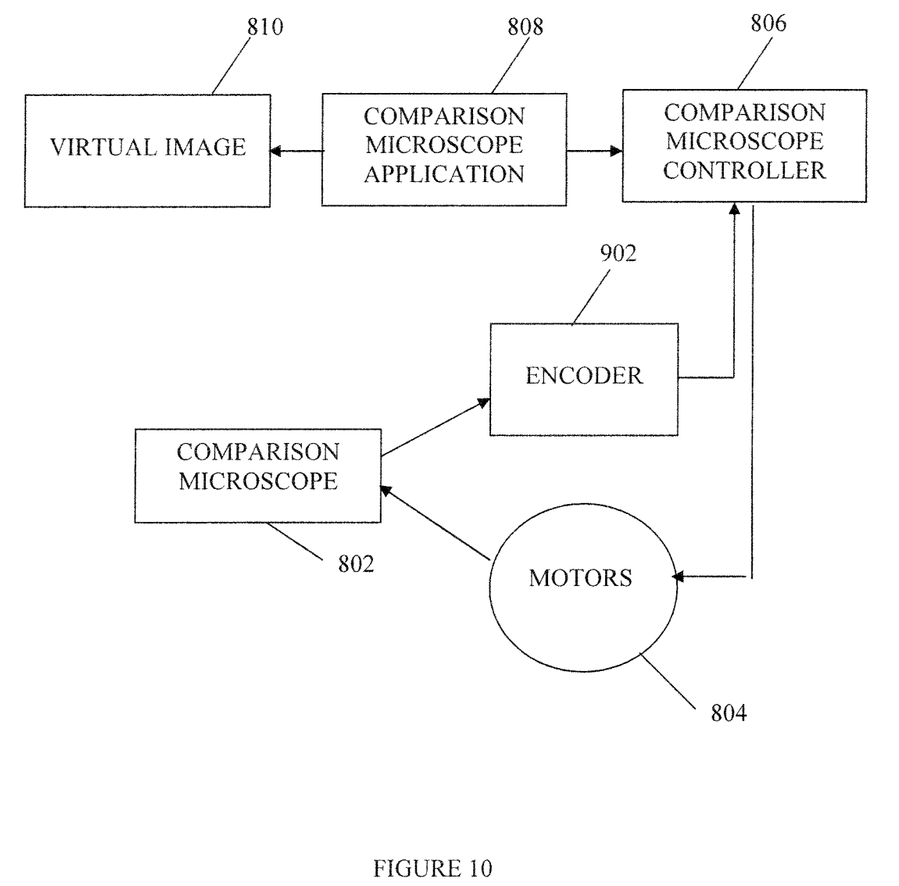
FIG. 10 is a block diagram illustrating a dual mode system.

FIG. 10 illustrates a dual mode system which allows both previous scenarios. This combination includes encoders 902 and motors 804 and allows the user to switch between the hybrid manual/automated mode and the fully automated mode at will.

It should be understood that the computer-implemented methods may be carried out using instructions and statements in a single application or a combination of two or more applications coupled to the processor 506. While illustrated in the block diagrams of FIGS. 5 and 8-10 as groups of discrete components communicating with each other via distinct data signal connections, it will be understood by those skilled in the art that the embodiments are provided by a combination of hardware and software components, with some components being implemented by a given function or operation of a hardware or software system, and many of the data paths illustrated being implemented by data communication within a computer application or operating system. The structure illustrated is thus provided for efficiency of teaching the present embodiments.

The embodiments of the invention described above are intended to be exemplary only. The scope of the invention is therefore intended to be limited solely by the scope of the appended claims.

We claim:

1. A computer-implemented method for analyzing at least one object under
a first microscope and a second microscope the method comprising:
receiving a first set of position coordinates of the at least one object under the first microscope as a set of features taken from 3D topographic data of a surface of the at least one object are successively displayed within a field of view thereof, the first microscope having a first coordinate system;
receiving a second set of position coordinates of the at least one object under the second microscope as a set of features taken from 3D topographic data of the surface of the at least one object are successively displayed within a field of view thereof, the second microscope having a second coordinate system;
computing a transformation to link the first coordinate system and the second coordinate system using the first set of position coordinates and the second set of position coordinates and irrespectively of an initial positioning of the at least one object under a respective one of the first microscope and the second microscope;
generating guidance data when one of the first microscope and the second microscope is displaced, the guidance data corresponding to a set of operations to be applied to the other of the first microscope and the second microscope to follow movement of the one of the first microscope and the second microscope for bringing the set of features displayed within the field of view of the first microscope to match the set of features displayed within the field of view of the second microscope; and
wherein the first microscope is a physical microscope and the second microscope is a virtual microscope, and wherein receiving a second set of position coordinates of the at least one object under the second microscope comprises receiving a set of coordinates for a set of features in an image of the at least one object on the virtual microscope.

2. The computer-implemented method of claim 1, further comprising:
acquiring 3D topographic data representative of a 3D surface topography of the object;
generating the image of the at least one object from the 3D topographic data; and displaying the image on the virtual microscope.

3. The computer-implemented method of claim 1, further comprising applying the guidance data to at least one of the physical microscope and the virtual microscope in an automated manner.

4. The computer-implemented method of claim 1, further comprising providing the guidance data to a user in a format allowing it to be applied manually.

5. The computer-implemented method of claim 4, wherein the format comprises one of translation/rotation steps for the physical microscope, graphical information, and physical indicators.

6. A system for analyzing at least one object microscopically, the system comprising:
at least a first microscope and a second microscope, the first microscope having a first coordinate system and the second microscope having a second coordinate system;
a computer system comprising a processor and a memory; and a microscope linking module stored on the memory and executable by the processor, the microscope linking module having program code that when executed, computes a transformation to link the first coordinate system and the second coordinate system irrespectively of an initial positioning of the at least one object under a respective one of the first microscope and the second microscope, and generates guidance data when one of the first microscope and the second microscope is displaced, the guidance data corresponding to a set of operations to be applied to the other of the first microscope and the second microscope to follow movement of the one of the first microscope and the second microscope for bringing a set of features taken from 3D topographic data of a surface of the at least one object displayed within the field of view of the first microscope to match a set of features taken from the 3D topographic data of the surface of the at least one object displayed within the field of view of the second microscope; and
wherein the first microscope is a physical microscope and the second microscope is a virtual microscope, and wherein receiving a second set of position coordinates of the at least one object under the second microscope comprises receiving a set of coordinates for a set of features in an image of the at least one object on the virtual microscope.

7. The system of claim 6, further comprising a data module stored on the memory and executable by the processor, the data module having program code that when executed, acquires 3D topographic data representative of a 3D surface topography of the at least one object, generates an image from the 3D topographic data, and displays the image on the virtual microscope.

8. The system of claim 6, further comprising a control module stored on the memory and executable by the processor, the control module having program code that when executed, applies the guidance data to at least one of the physical microscope and the virtual microscope in an automated manner.

9. The system of claim 6, further comprising a control module stored on the memory and executable by the processor, the control module having program code that when executed, provides the guidance data to a user in a format allowing it to be applied manually.

10. A non-transitory computer readable memory having recorded thereon statements and instructions for execution by a computer to implement a method for analyzing at least one object under a first microscope and a second microscope and carry out the steps of:

receiving a first set of position coordinates of the at least one object under the first microscope as a set of features taken from 3D topographic data of a surface of the at least one object are successively displayed within a field of view thereof, the first microscope having a first coordinate system;

receiving a second set of position coordinates of the at least one object under the second microscope as a set of features taken from 3D topographic data of the surface of the at least one object are successively displayed within a field of view thereof, the second microscope having a second coordinate system;

computing a transformation to link the first coordinate system and the second coordinate system using the first set of position coordinates and the second set of position coordinates and irrespectively of an initial positioning of the at least one object under a respective one of the first microscope and the second microscope;

generating guidance data when one of the first microscope and the second microscope is displaced, the guidance data corresponding to a set of operations to be applied to the other of the first microscope and the second microscope to follow movement of the one of the first microscope and the second microscope for bringing the set of features displayed within the field of view of the first microscope to match the set of features displayed within the field of view of the second microscope; and wherein the first microscope is a physical microscope and the second microscope is a virtual microscope, and wherein receiving a second set of position coordinates of the at least one object under the second microscope comprises receiving a set of coordinates for a set of features in an image of the at least one object on the virtual microscope.

* * * * *